United States Patent
Chang et al.

(10) Patent No.: US 10,865,277 B2
(45) Date of Patent: Dec. 15, 2020

(54) METHOD FOR MANUFACTURING A METAL NANOSTRUCTURE HAVING A CHIRAL STRUCTURE COMPRISING REGIOSELECTIVITY ADSORBING A PEPTIDE ON THE SURFACE OF A METAL SEED PARTICLE

(71) Applicants: LG Display Co., Ltd., Seoul (KR); SNU R&DB Foundation, Seoul (KR)

(72) Inventors: KiSeok Chang, Paju-si (KR); WookSung Kim, Goyang-si (KR); KiTae Nam, Seoul (KR); SungPil Ryu, Paju-si (KR); HyeEun Lee, Seoul (KR); HyoYong Ahn, Seoul (KR)

(73) Assignees: LG Display Co., Ltd., Seoul (KR); SNU R&DB Foundation, Seoul (KR)

( * ) Notice: Subject to any disclaimer, the term of this patent is extended or adjusted under 35 U.S.C. 154(b) by 158 days.

(21) Appl. No.: 15/965,726

(22) Filed: Apr. 27, 2018

(65) Prior Publication Data

US 2018/0312636 A1    Nov. 1, 2018

Related U.S. Application Data

(60) Provisional application No. 62/491,825, filed on Apr. 28, 2017.

(51) Int. Cl.
*C30B 7/14*    (2006.01)
*C08G 73/02*    (2006.01)
(Continued)

(52) U.S. Cl.
CPC ........ *C08G 73/0206* (2013.01); *B22F 1/0018* (2013.01); *B22F 9/24* (2013.01);
(Continued)

(58) Field of Classification Search
CPC .. C30B 7/00; C30B 7/14; C30B 19/00; C30B 19/10; C30B 19/12; C30B 29/00;
(Continued)

(56) References Cited

U.S. PATENT DOCUMENTS 9,701,545 B2    7/2017   Jin et al.
2013/0008690 A1  1/2013   Wiley et al.
(Continued)

FOREIGN PATENT DOCUMENTS

CN    106238728 A  * 12/2016
CN    106238728 A    12/2016
(Continued)

OTHER PUBLICATIONS

Ben-Moshe, et al. publication entitled "Enantioselective control of lattice and shape chirality in inorganic nanostructures using chiral biomolecules," Nature Communications, vol. 5, p. 4302 (2014). (Year: 2014).*
(Continued)

*Primary Examiner* — Kenneth A Bratland, Jr.
(74) *Attorney, Agent, or Firm* — Fenwick & West LLP

(57) ABSTRACT

The present disclosure relates to a method for manufacturing a metal nanostructure having a chiral structure. The method for manufacturing a metal nanostructure comprises: preparing a first mixture solution by mixing a metal precursor, a surfactant, and a reducing agent; preparing a second mixture solution by adding a peptide to the first mixture solution; and preparing a metal nanostructure having a chiral structure by adding a metal seed particle to the second mixture solution.

7 Claims, 21 Drawing Sheets

(51) Int. Cl.
| | |
|---|---|
| *B22F 1/00* | (2006.01) |
| *B22F 9/24* | (2006.01) |
| *C07K 5/078* | (2006.01) |
| *C07K 5/062* | (2006.01) |
| *C07K 5/02* | (2006.01) |
| *B82Y 40/00* | (2011.01) |
| *B82Y 20/00* | (2011.01) |
| *B82Y 30/00* | (2011.01) |

(52) U.S. Cl.
CPC ........ *C07K 5/0215* (2013.01); *C07K 5/06026* (2013.01); *C07K 5/06165* (2013.01); *C30B 7/14* (2013.01); *B22F 2001/0037* (2013.01); *B82Y 20/00* (2013.01); *B82Y 30/00* (2013.01); *B82Y 40/00* (2013.01); *Y10S 977/895* (2013.01)

(58) Field of Classification Search
CPC ... C30B 29/60; C30B 29/607; C08G 73/0206; B22F 1/0018; B22F 9/24; B22F 2001/0037; C07K 5/0215; C07K 5/06026; C07K 5/06165; B82Y 20/00; B82Y 30/00; B82Y 40/00
USPC ............ 117/11, 54, 56, 63–64, 68, 902, 923
See application file for complete search history.

(56) References Cited

U.S. PATENT DOCUMENTS

| | | |
|---|---|---|
| 2014/0299821 A1 | 10/2014 | Rudhardt et al. |
| 2016/0263931 A1 | 9/2016 | Garnier et al. |

FOREIGN PATENT DOCUMENTS

| | | |
|---|---|---|
| JP | 2005-239863 A | 9/2005 |
| JP | 2014-133689 A | 7/2014 |
| JP | 5958842 B2 | 8/2016 |
| KR | 10-0900876 B1 | 6/2009 |
| KR | 10-2012-0115298 A | 10/2012 |
| KR | 10-2014-0093704 A | 7/2014 |
| KR | 10-2016-0070745 A | 6/2016 |

OTHER PUBLICATIONS

Jung, A. et al., "Synthesis of 3D Chiral Nanostructures and their Applications," Polymer Science and Technology, vol. 27, No. 6, Dec. 2016, pp. 782-787.
PCT International Search Report, PCT Application No. PCT/KR2018/004932, dated Jul. 25, 2018, three pages.
PCT International Search Report, PCT Application No. PCT/KR2018/004933, dated Jul. 27, 2018, three pages.
Sau, T. et al., "Size Controlled Synthesis of Gold Nanoparticles Using Photochemically Prepared Seed Particles," Journal of Nanoparticle Research, vol. 3, Iss. 4, Aug. 2001, pp. 257-261.

\* cited by examiner (a)            (b)

(a)            (b)

(a) (b)

(a)

(b)

(a)

(b)

(a)

(b)

(a)

(b)

(a)

(b)

METHOD FOR MANUFACTURING A METAL NANOSTRUCTURE HAVING A CHIRAL STRUCTURE COMPRISING REGIOSELECTIVITY ADSORBING A PEPTIDE ON THE SURFACE OF A METAL SEED PARTICLE

CROSS-REFERENCE TO RELATED APPLICATIONS

This application claims the priority of U.S. Provisional Application No. 62/491,825 filed on Apr. 28, 2017, in the United States Patents and Trademark Office, the disclosure of which is incorporated herein by reference in its entirety.

BACKGROUND

Field

The present disclosure relates to a metal nanostructure and a manufacturing method thereof, and more particularly, to a method for manufacturing a metal nanostructure having a chirality.

Description of the Related Art

A chiral structure refers to a material having a three-dimensional chiral structure. The three-dimensional chiral structure is not limited thereto, but it means an asymmetric structure which is twisted in one direction. Therefore, the chiral structure has a structure which is grown to be bent in one direction.

The chiral structure may be formed by an organic or inorganic compound or may be formed by a metal compound.

A method for creating chiral structures of the related art is mainly divided into a top down type and a bottom up type. For example, the top down type includes electron-beam lithography, a glancing angle deposition method, or a direct laser writing method. The bottom up type includes a method of assembling particles using an organic molecule such as DNA or peptide. However, according to the technique of the related art, a time and a manufacturing cost are high and a yield is low so that it is not appropriate for mass production and it is very restrictive to implement and adjust optical characteristic in a visible light region.

More specifically, the electron-beam lithography method is a method optimized for manufacturing a theoretically designed structure and various designs using this technique have been proposed. Further, a method of laminating several layers designed by the electron-beam lithography has been proposed to increase a coupling strength. However, the electron beam lithography method is very costly and cannot be applied for mass production.

Next, the direct laser writing method and the glancing angle deposition method are mainly used to create uniaxial gold helix so that a desired design may be created. However, the direct laser writing method and the glancing angle deposition method are very costly and cannot be applied for mass production.

Next, a method using helical template is a method of removing a template after depositing a metal using a helical polymer or liquid crystal as a template. However, according to this method, it is difficult to manufacture well-defined uniform structure.

Next, a method using a chiral molecule is a method of creating a chiral nanostructure by inducing a chiral assembly of nanoparticles using a chiral organic molecule such as a designed long range DNA and has a very low yield.

Specifically, in order to be applied for the display device and an optical device, a chiral nanostructure having a high optical activity in a visible light range is required and thus control in a nanometer (nm) level is necessary. However, the top down type of the related art has lots of restrictions for the nanometer level control due to a resolution of the device, so that structures having an optical activity in an infrared (IR) range having a relatively long wavelength have been mainly reported.

The chiral structure manufactured by the method of the related art has a rigid nano/micro structure pattern so that a large thickness is required to have an optical activity. Therefore, the flexibility is deteriorated. However, a technique which implements the flexibility or a film type having various sizes or shapes is necessary to be utilized for various products.

SUMMARY

An object to be achieved by the present disclosure is to provide a method for manufacturing a nano-sized chiral metal nanostructure.

The present disclosure is a novel bottom up type synthesizing method which is capable of manufacturing a new chiral nanostructure by introducing peptide.

The present disclosure provides a chiral metal nanostructure having an optical activity (g-factor) which is ten times higher than a particle of the related art in a visible light region.

The present disclosure provides a method for synthesizing a chiral metal nanostructure having various optical characteristics by a solution process at a room temperature without using an expensive deposition equipment which is used for the related art or without having complexity.

Objects of the present disclosure are not limited to the above-mentioned objects, and other objects, which are not mentioned above, can be clearly understood by those skilled in the art from the following descriptions.

According to an aspect of the present disclosure, a manufacturing method of a metal nanostructure comprises: preparing a first mixture solution by mixing a metal precursor, a surfactant, and a reducing agent; preparing a second mixture solution by adding a peptide to the first mixture solution; and preparing a metal nanostructure having a chiral structure by adding a metal seed particle to the second mixture solution to grow the metal.

According to another aspect of the present disclosure, a metal nanostructure has a chiral structure and a particle size of 10 nm to 500 nm.

Other detailed matters of the embodiments are included in the detailed description and the drawings.

According to the present disclosure, the present disclosure may provide a manufacturing method which is capable of synthesizing a novel chiral metal nanostructure having a high optical activity in a visible light region and massively synthesizing a uniform chiral metal nanostructure at a room temperature by an economical method while systematically controlling the optical activity.

According to the present disclosure, several types of chiral structures may be synthesized using various types of peptides.

According to the manufacturing method of the related art, one type of chiral structure can be synthesized by one method. However, according to the manufacturing method of a chiral metal structure of the present disclosure, a chiral structure having various structures can be massively synthesized by changing only the peptide during the same synthesizing process.

The effects according to the present invention are not limited to the contents exemplified above, and more various effects are included in the present specification.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION

Figure 1:
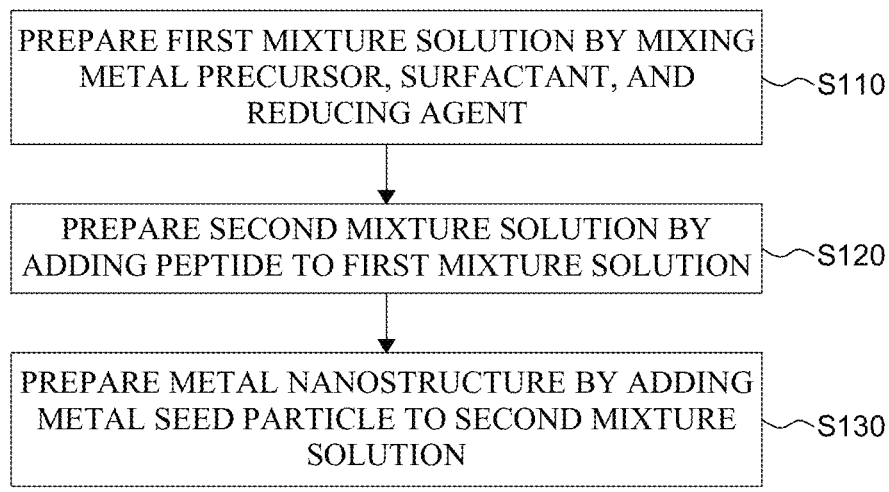
FIG. 1 is a flowchart for explaining a manufacturing method of a chiral metal nanostructure according to an exemplary embodiment of the present disclosure.

Advantages and characteristics of the present disclosure and a method of achieving the advantages and characteristics will be clear by referring to exemplary embodiments described below in detail together with the accompanying drawings. However, the present disclosure is not limited to the following exemplary embodiments but may be implemented in various different forms. The exemplary embodiments are provided only to complete disclosure of the present disclosure and to fully provide a person having ordinary skill in the art to which the present disclosure pertains with the category of the disclosure, and the present disclosure will be defined by the appended claims.

The shapes, sizes, ratios, angles, numbers, and the like illustrated in the accompanying drawings for describing the exemplary embodiments of the present disclosure are merely examples, and the present disclosure is not limited thereto. Like reference numerals generally denote like elements throughout the present specification. Further, in the following description, a detailed explanation of known related technologies may be omitted to avoid unnecessarily obscuring the subject matter of the present disclosure. The terms such as "including," "having," and "consist of" used herein are generally intended to allow other components to be added unless the terms are used with the term "only". Any references to singular may include plural unless expressly stated otherwise.

Components are interpreted to include an ordinary error range even if not expressly stated.

When the position relation between two parts is described using the terms such as "on", "above", "below", and "next", one or more parts may be positioned between the two parts unless the terms are used with the term "immediately" or "directly" is not used.

When an element or layer is disposed "on" another element or layer, another layer or another element may be interposed directly on the other element or therebetween.

Although the terms "first", "second", and the like are used for describing various components, these components are not confined by these terms. These terms are merely used for distinguishing one component from the other components. Therefore, a first component to be mentioned below may be a second component in a technical concept of the present disclosure.

Like reference numerals generally denote like elements throughout the specification.

A size and a thickness of each component illustrated in the drawing are illustrated for the convenience of description, and the present disclosure is not limited to the size and the thickness of the component illustrated.

The features of various embodiments of the present disclosure can be partially or entirely bonded to or combined with each other and can be interlocked and operated in technically various ways, and the embodiments can be carried out independently of or in association with each other.

Hereinafter, the present disclosure will be described in detail with reference to the drawings.

Figure 2:
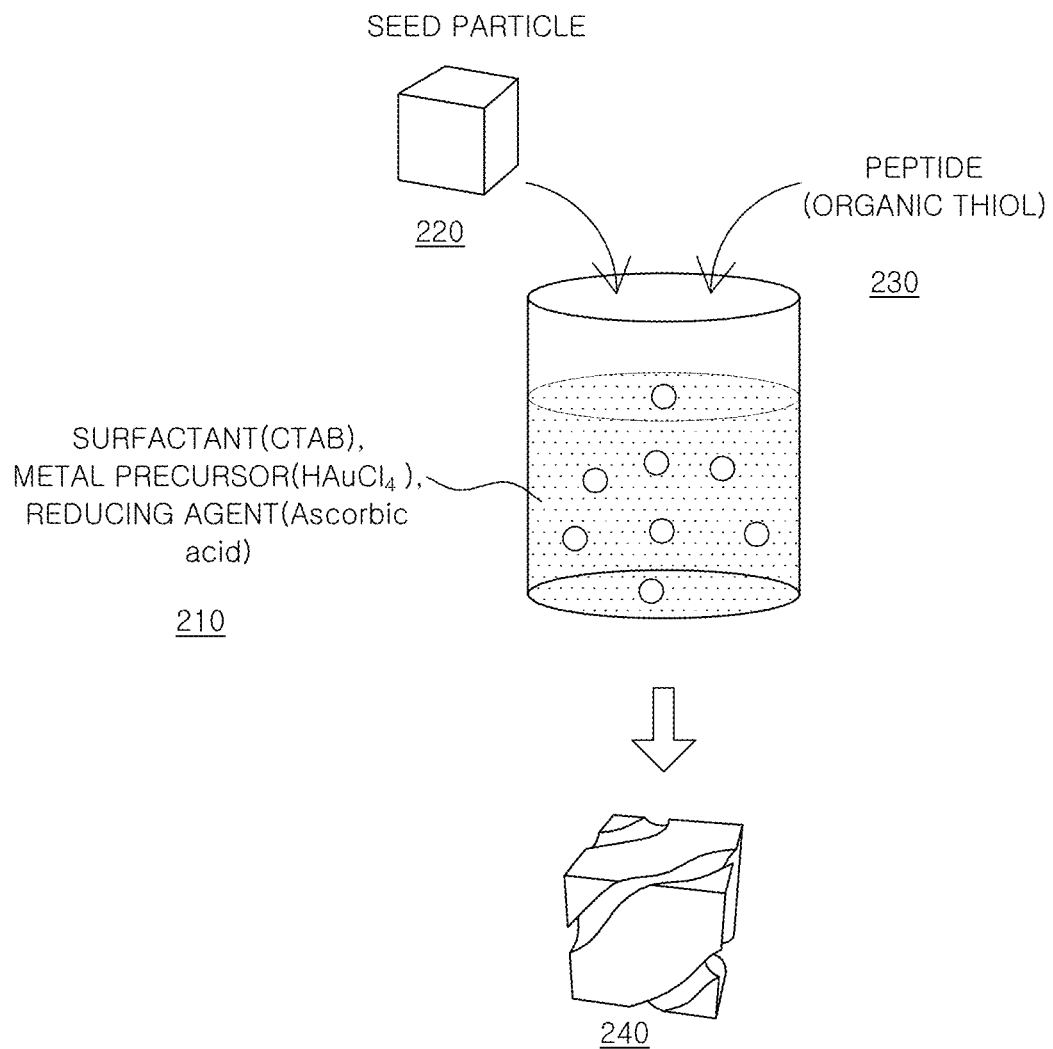
FIG. 2 is a schematic view for schematically explaining a manufacturing method of a chiral metal nanostructure according to an exemplary embodiment of the present disclosure.

FIG. 1 is a flowchart for explaining a manufacturing method of a chiral metal nanostructure according to an exemplary embodiment of the present disclosure. FIG. 2 is a schematic view for schematically explaining a manufacturing method of a chiral metal nanostructure according to an exemplary embodiment of the present disclosure.

Referring to FIG. 1, a manufacturing method of a chiral metal nanostructure according to an exemplary embodiment of the present disclosure includes a step S110 of preparing a first mixture solution by mixing a metal precursor, a surfactant, and a reducing agent, a step S120 of preparing a second mixture solution by adding peptide to the first mixture solution, and a step S130 of preparing a chiral metal nanostructure by adding a metal seed particle to the second mixture solution to grow the metal.

First, the metal precursor, the surfactant, and the reducing agent are mixed to prepare the first mixture solution (S110). Specifically, the step of preparing a first mixture solution may include a step of preparing a solution containing a surfactant, a step of mixing the metal precursor and the reducing agent to the solution, and a step of blending using a vortex mixer.

The metal precursor is a material which is reduced by the reducing agent to form a metal particle. Any metal material which is capable of forming a nano-sized metal nanostructure using a seed mediated growth method can be used without limitation. For example, the metal precursor may be formed of a precursor containing a metal material such as gold, silver, or copper, but is not limited thereto. For example, when a metal nanostructure is formed using gold as a metal material, chloroauric acid ($HAuCl_4$) may be used as the metal precursor.

The surfactant is adsorbed on a metal seed particle to form a bilayer and thus serves as a soft template. Materials used in the technical field may be used as the surfactant. For example, the surfactant may include any one selected from the group consisting of cetyltrimethylammonium bromide (CTAB), cetyltrimethylammonium chloride (CTAC), cetylpyridinium chloride (CPC), and polyvinylpyrrolidone (PVP), but is not limited thereto.

The reducing agent reduces the metal ion of the metal precursor and grows the metal on the metal seed particle to be described later. The reducing agent may use, for example, ascorbic acid or a material having an oxidation potential equivalent to that of ascorbic acid, for example, hydroxylamine, hydroquinone, or succinic acid, but is not limited thereto.

Next, the peptide is added to the first mixture solution to prepare a second mixture solution (S120).

The peptide asymmetrically grows the metal particles on the metal seed particles to be described below to form a metal nanostructure having a chiral structure. Specifically, the peptide is adsorbed on a specific surface among a plurality of surfaces (crystal faces) of the metal seed particle and then suppresses the metal ion from being attached on a surface of the metal seed particle to be grown by the reduction of the metal precursor. That is, a speed of growing the metal on a surface of the metal seed particle on which the peptide is adsorbed and on the other surface of the metal seed particle on which the peptide is not adsorbed is controlled to form the metal nanostructure having a chiral structure.

The peptide is a structure containing an amino group and a carboxyl group. Peptides include a monopeptide, which is an amino acid containing one amino group and one carboxyl group, a dipeptide formed by bonding two or more amino acids, and a tripeptide formed by bonding three or more amino acids. Further, the peptide may be an oligopeptide formed by binding less than ten amino acids or a polypeptide formed by binding ten or more amino acids depending on the number of amino acids, but is not limited thereto.

For example, the peptide may include one or more selected from the group consisting of cysteine (Cys), glutamate (Glu), alanine (Ala), glycine (Gly), penicillamine, histidine, lysine, ornithine, arginine, aspartic acid, glutamic acid, asparagine, glutathione, and glutamine, but is not limited thereto. In the meantime, the peptide may include both D- and L-forms which are enantiomers.

The peptide may further include a thiol group (—SH). Specifically, the peptide may have a structure containing the thiol group in a side chain of the amino acid. For example, the peptide containing a thiol group may be cysteine or glutathione, but is not limited thereto.

The thiol group improves an adsorptive power between the peptide and the surface of the metal seed particle. That is, the peptide containing a thiol group is well adsorbed onto the surface of the metal seed particle and thus the metal may be grown so as to have a chiral structure.

The peptide may be adsorbed on the surface of the metal seed particle. More specifically, the amino group of the peptide may form a physical bond with the surface of the metal seed particle. The peptide has a chiral structure having enantiomers and has different optical properties depending on whether it is a D-form or an L-form. The peptide having a chiral structure is selectively adsorbed on different surfaces of the metal seed particle depending on whether it is a D-form or an L-form.

Next, the metal seed particle is added to the second mixture solution to prepare a metal nanostructure (S130).

The metal seed particle is a metal material having a nanometer (nm) size and is used as a starting material for forming a chiral metal nanostructure.

Any metal material which is capable of forming a nano-sized metal structure using a seed mediated growth method may be used for the metal seed particle without limitation. The metal seed particle is formed of a metal material such as gold, silver, or copper and may be formed of the same material as the metal precursor, but is not limited thereto.

The size of the metal seed particle may be 1 nm to 100 nm, but is not limited thereto. Further, the metal seed particle may have various shapes. For example, the metal seed particle may be a nanoparticle having a shape having a high Miller index crystal face such as a hexoctahedron or may be a nanoparticle having a shape having a low Miller index crystal face such as cube, octahedron, rhombic dodecahedron, or cuboctahedron.

The crystal face of a high Miller index refers to a crystal face satisfying a condition that a Miller index $\{hkl\}$ indicating a characteristic of the nanoparticle crystal face is $h>k>l>0$. In contrast, a low Miller index crystal face may be a crystal face having a Miller index of $\{100\}$, $\{111\}$, and $\{110\}$ as an example. The crystal face of the high Miller index may be formed by a sum of integer multiples of the low Miller index crystal faces. The nanoparticles formed of the high Miller index crystal faces generally have twenty or more faces exposed to one particle and a curvature at the corner or vertex at which crystal faces are coupled to each other may be larger than that of the low Miller index crystal faces.

The metal seed particle may be prepared by a seed mediated growth method which is one of colloidal synthesis methods, but is not limited thereto. For example, the seed mediated growth method may reduce the precursor using a reducing agent in the presence of a surfactant to form the metal seed particle.

The chiral metal nanostructure is formed through the step S130. Since the peptide present in the second mixture solution has a chiral property, when the metal seed particle is added to the second mixture solution, the peptide is regioselectively adsorbed on the surface of the metal seed particle. Thereafter, the metal is grown on the surface of the metal seed particle while reducing the metal precursor. In this case, the growth speed of the metal varies in every position, due to the peptide which is selectively adsorbed on the surface of the metal seed particle. That is, the metal growth speed is low on the surface of the metal seed particle on which a large amount of peptide is adsorbed and the metal growth speed is relatively high on the surface of the metal seed particle on which a small amount of peptide is adsorbed or no peptide is adsorbed. Due to the difference of metal growth speeds between adjacent surfaces of the metal seed particle, the metal may be grown while being bent in a predetermined direction. By doing this, a three-dimensional chiral structure which is twisted in one direction is formed.

Hereinafter, a method for manufacturing a chiral metal nanostructure of the present disclosure will be described in more detail through examples. The structure will be described to be more specifically with reference to FIGS. 3A to 3D. However, the following examples are set forth to illustrate the present disclosure, but the scope of the disclosure is not limited thereto.

Example 1

0.8 mL of hexadecyltrimethylammonium bromide (CTAB) which was a surfactant having a concentration of 100 mM was added into 3.95 mL of water. 0.1 mL of 10 mM tetrachloroauric (III) trihydrate ($HAuCl_4$ $3H_2O$) which was a gold precursor and 0.475 mL of 0.1 M L-ascorbic acid which was a reducing agent were mixed with the above solution and then blended by a vortex mixer for one minute to prepare a first mixture solution. 0.5 μL of 1 mM L-cysteine dissolved in water was added to the prepared first mixture solution 210, and then blended by the vortex mixer for 1 minute to prepare a second mixture solution. The growth started by adding a cube nanoparticle 220 having a size of 45 nm to the second mixture solution 210 and then two hours later, a metal nanostructure 240 having a chiral structure controlled by the L-cysteine was synthesized. Thereafter, the resulting metal nanostructure was washed and separated through centrifugation (5000 rpm for 30 seconds).

The method for manufacturing a metal nanostructure 240 having a chiral structure according to one exemplary embodiment of the present disclosure may undergo an intermediate step in which the cubic metal particle having a low Miller index crystal face used as the metal seed particle 220 is grown to the hexoctahedron having a high Miller index crystal face. That is, when the cube metal seed particle 220 having a size of 45 nm was injected into the second mixture solution, the peptide 230 was not immediately adsorbed on the surface of the metal seed particle 220, but the metal was grown on the surface of the cube metal seed particle 220 to form the hexoctahedron metal particle as an intermediate. Therefore, the peptide 230 was adsorbed on the surface of the hexoctahedron metal particle which was an intermediate to be grown as a metal nanostructure 240 having a chiral structure. Hereinafter, a process of forming a metal nanostructure 240 having a chiral structure from the hexoctahedron metal particle which is an intermediate will be described.

Figure 3A:
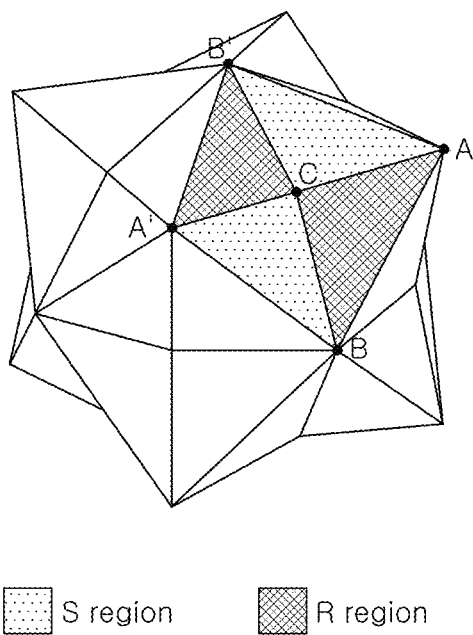
FIGS. 3A to 3D are schematic diagrams and SEM images for explaining a process of forming a chiral metal nanostructure according to Example 1 of the present disclosure.
Figure 3B:
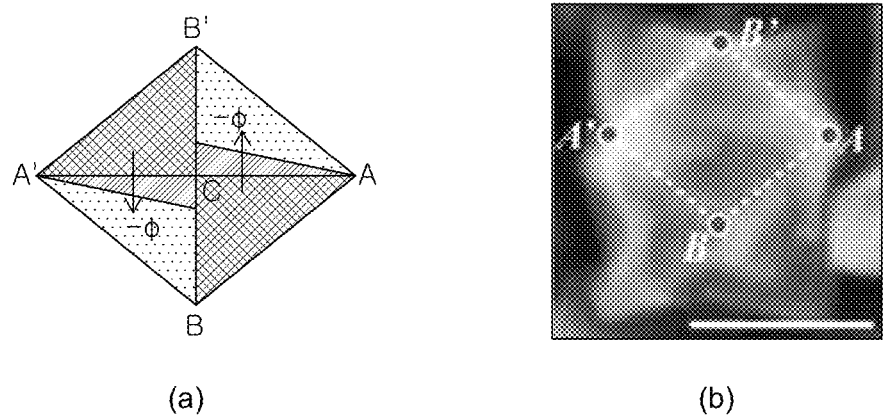
Figure 3C:
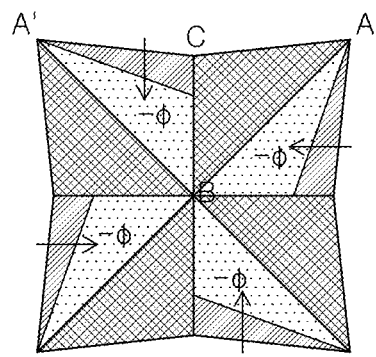
Figure 3C:
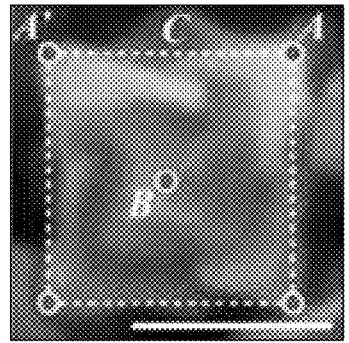
Figure 3D:
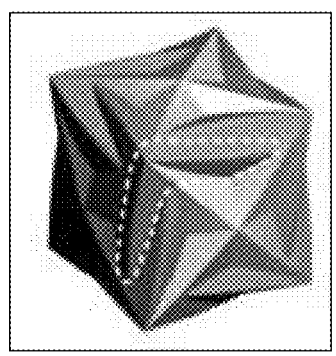
Figure 3D:
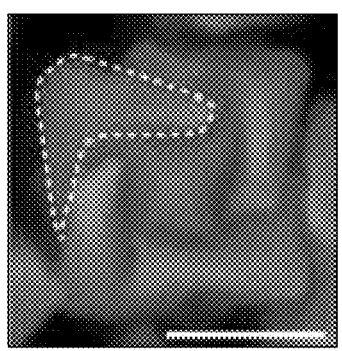

FIGS. 3A to 3D are schematic diagrams and SEM images for explaining a process of forming a chiral metal nanostructure according to Example 1. FIG. 3A is a schematic diagram illustrating the hexoctahedron metal particle which is an intermediate which is formed during the process of forming a chiral metal nanostructure from the cube metal seed particle. FIGS. 3B and 3C are a schematic diagram and an SEM image seen from {110} and {100} directions for explaining a behavior of a hexoctahedron metal particle surface in the presence of L-cysteine. FIG. 3D is a schematic diagram and an SEM image for explaining a structure of a chiral metal nanostructure prepared by Example 1.

Referring to FIG. 3A, the hexoctahedron metal particle has a structure enclosed by 48 surfaces having a same size triangular shape and has a high Miller index of {321}. In this case, referring to ABB'A' region, the {321} plane and {231} plane are configured by an R region with a clockwise rotation and an S region with a counterclockwise rotation. The R region and the S region have chirality and may be symmetric to each other with respect to a boundary line. The hexoctahedron metal particle has 24 R regions and 24 S regions to have achirality with respect to the entire metal particle. In this case, the L-cysteine is known to prefer the R region. When the metal seed particle is added to the second mixture solution, the L-cysteine is mainly adsorbed in the R region of the metal seed particle. Since the L-cysteine mainly occupies the surface of the R region of the metal seed particle, the metal growth speed of the R region is slower than the metal growth speed of the S region.

FIGS. 3B and 3C illustrate a schematic diagram of ABA'B' region configured by two sets of R region and S region and an SEM image in which an area corresponding to the ABA'B' region is represented by the dotted line. Referring to FIG. 3B, the growth of the metal which is transformed at AC and CA' among boundaries of the S region and R region is identified. The transformed metal may be grown at all boundaries of the hexoctahedron. Both the straight lines AC and CA' indicating the boundaries are −φ and are twisted to protrude into the S region. As described above, since the growth of the metal is suppressed by the L-cysteine adsorbed on the surface of the R region, the metal is grown to be directed to the S region at the boundary of the S region and the R region. Therefore, the twisted corner continuously extends toward the inside of the S region.

Referring to FIG. 3D, the chiral metal nanostructure formed by Example 1 has a helicoid shape having a structure in which the corners are twisted to the inner surface.

The method for manufacturing a metal nanostructure according to the exemplary embodiment of the present disclosure may form a nano-sized metal structure having a chiral structure.

Specifically, the metal nanostructure manufactured by the method for manufacturing a metal nanostructure according to the exemplary embodiment of the present disclosure has a three-dimensional chiral structure. The chiral structure means a structure in which enantiomers do not overlap each other. For example, the metal nanostructure having a chiral structure may have a shape which is twisted in one direction. That is, a corner of the metal nanostructure is bent in one direction. For example, the metal nanostructure may have a helicoid shape in which the corner is twisted in one direction.

Further, the metal nanostructure may be formed of a concave portion and a convex portion. In this case, the concave portion may be formed to be connected to an adjacent surface. Specifically, the concave portion may be formed to be connected to two or more surfaces and may be formed to be connected to only two surfaces.

Further, the metal nanostructure may include the convex portion which extends to be bent in the same direction with respect to vertexes. The convex portion is formed such that a corner extending from each vertex of the metal nanostructure extends to be twisted in one direction. Therefore, a pinwheel shaped convex portion may be formed.

A size of the metal nanostructure according to the exemplary embodiment of the present disclosure may be 10 nm to 500 nm, and desirably, may be 50 nm to 300 nm, but is not limited thereto. The method for manufacturing a metal nanostructure according to the exemplary embodiment of the present disclosure is advantageous to manufacture a nano-sized metal structure which has a chiral structure.

A specific shape of the metal nanostructure will be described in more detail in the following Examples.

Since the metal nanostructure according to the exemplary embodiment of the present disclosure has a chiral structure, individual metal nanostructures may have different optical characteristics. Specifically, the metal nanostructures having different chiral structures may have different light absorption regions for visible light, different polarization characteristics, and different optical activities (g-factors).

Hereinafter, in the method for manufacturing a chiral metal nanostructure according to one exemplary embodiment of the present disclosure described above, factors which may affect the structure and the optical properties of the prepared chiral metal nanostructure will be described in more detail.

1. Type of Peptide

In the method for manufacturing a chiral metal nanostructure according to one exemplary embodiment of the present disclosure, the chiral structure and the optical characteristic of the prepared chiral metal nanostructure were changed depending on the type of peptide. That is, the metal nanostructure having various chiral structures may be formed by changing the type of peptide to be used.

As described above, the peptide may include one or more selected from the group consisting of cysteine (Cys), alanine (Ala), glycine (Gly), penicillamine, histidine, lysine, ornithine, arginine, aspartic acid, glutamic acid, asparagine, and glutamine, but is not limited thereto. Further, the peptides include a monopeptide, which is formed of one amino acid, a dipeptide formed by bonding two or more amino acids, and a tripeptide formed by bonding three or more amino acids.

As described above, the metal nanostructure having different chiral structures may be formed depending on the type and the structure of peptide. In the case of the peptide formed of a plurality of amino acids, the structure of the chiral metal nanostructure may be controlled in various ways by a combination of various amino acids.

In order to describe a process of forming a metal nanostructure having different chiral structures depending on the type of peptide, a chiral metal nanostructure which was prepared using L-glutathione as a peptide was examined. The chiral metal nanostructure prepared using L-glutathione was prepared by a method according to Example 2.

Example 2

The chiral metal nanostructure was prepared by the same method as Example 1 except that L-glutathione was used instead of L-cysteine.

Figure 4A:
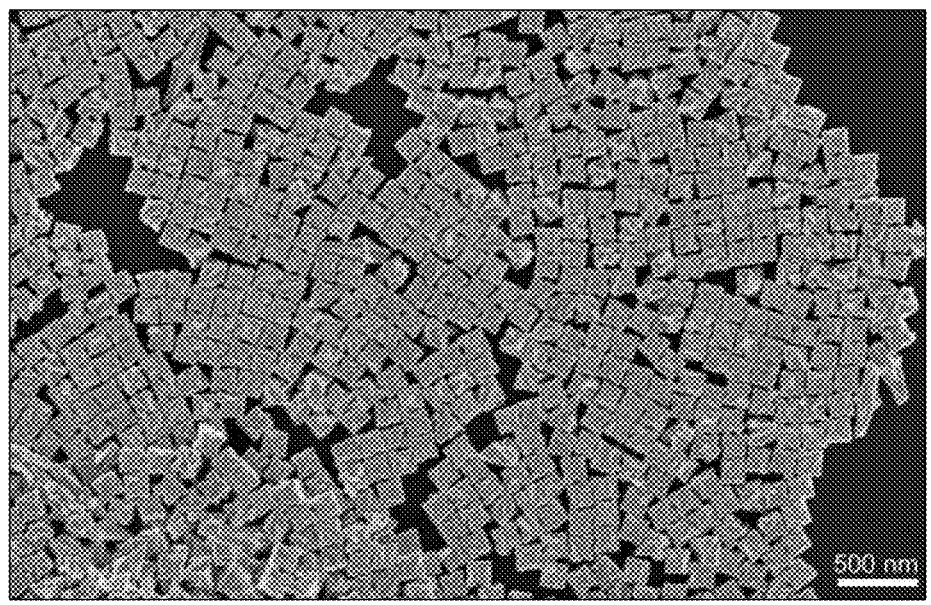
FIGS. 4A to 4D are schematic diagrams and SEM images for explaining a process of forming a chiral metal nanostructure according to Example 2 of the present disclosure.
Figure 4B:
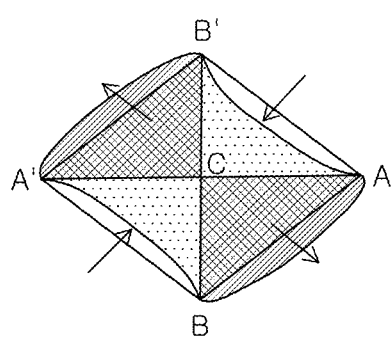
Figure 4B:
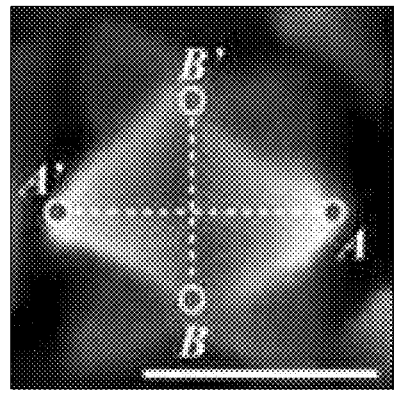
Figure 4C:
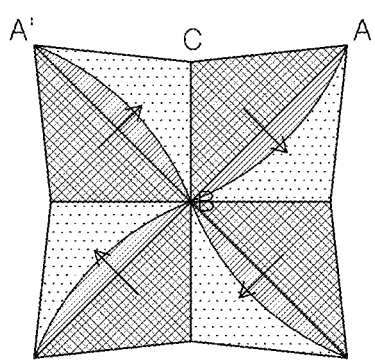
Figure 4C:
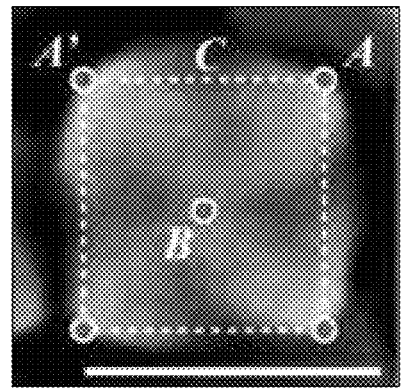
Figure 4D:
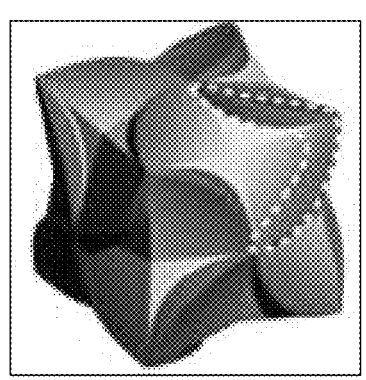
Figure 4D:
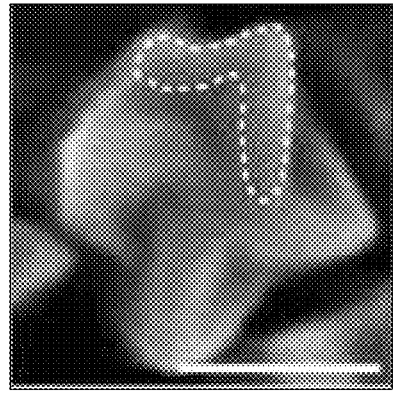

FIGS. 4A to 4D are schematic diagrams and SEM images for explaining a process of forming a chiral metal nanostructure according to Example 2. FIG. 4A is an SEM image of a chiral metal nanostructure prepared by Example 2. FIGS. 4B and 4C are a schematic diagram and an SEM image seen from {110} and {100} directions for explaining a behavior of a hexoctahedron metal particle surface which is an intermediate in the presence of L-glutathione. FIG. 4D is a schematic diagram and an SEM image for explaining a structure of a chiral metal nanostructure prepared by Example 2. The shape and the surface of the metal seed particles are the same as those described with reference to FIGS. 3A to 3D, so that a specific description will be omitted.

Referring to FIGS. 4B and 4C, L-glutathione is mainly adsorbed in the R region of the hexoctahedron metal particle which is an intermediate. Since the L-glutathione mainly occupies the surface of the R region of the metal seed particle, the metal growth speed of the R region is slower than the metal growth speed of the S region. In this case, referring to FIG. 4B viewed from {110} and {100} directions, the metal was grown at the boundaries A'B' and AB among the boundaries of the S region and the R region to outwardly expand and the metal was grown at the other boundaries A'B and B'A to inwardly move. Referring to FIG. 4C viewed from {100} direction, the metal was grown at the boundaries A'B' and AB to be directed to the S region. As a result, it was confirmed that the metal was grown to have a structure of a pinwheel.

As compared with Example 1 in which the metal nanostructure was prepared using the L-cysteine, L-glutathione which was a different peptide was used to form a metal nanostructure having a different chiral structure.

Further, a metal nanostructure prepared using various types of peptides will be confirmed with reference to FIGS. 5A to 5D.

Figure 5A:
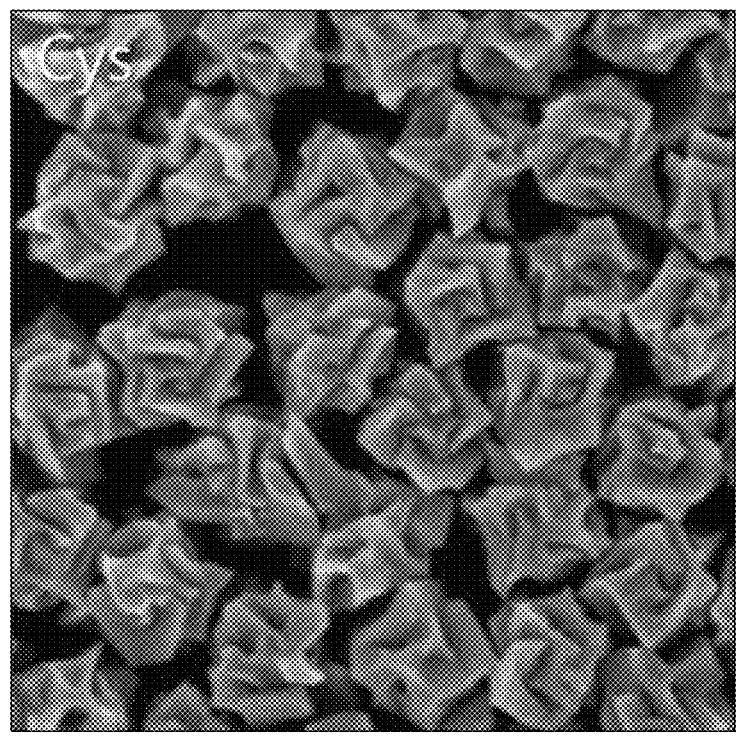
FIGS. 5A to 5D are SEM images and circular dichroism (CD) spectra of a chiral metal nanostructure manufactured using various types of peptides according to an embodiment of the present disclosure.
Figure 5A:
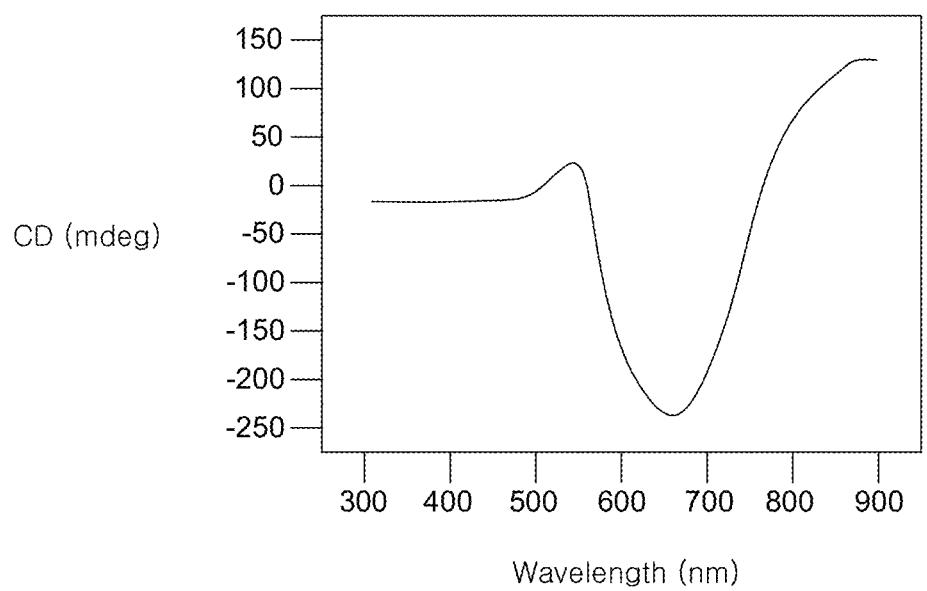
Figure 5B:
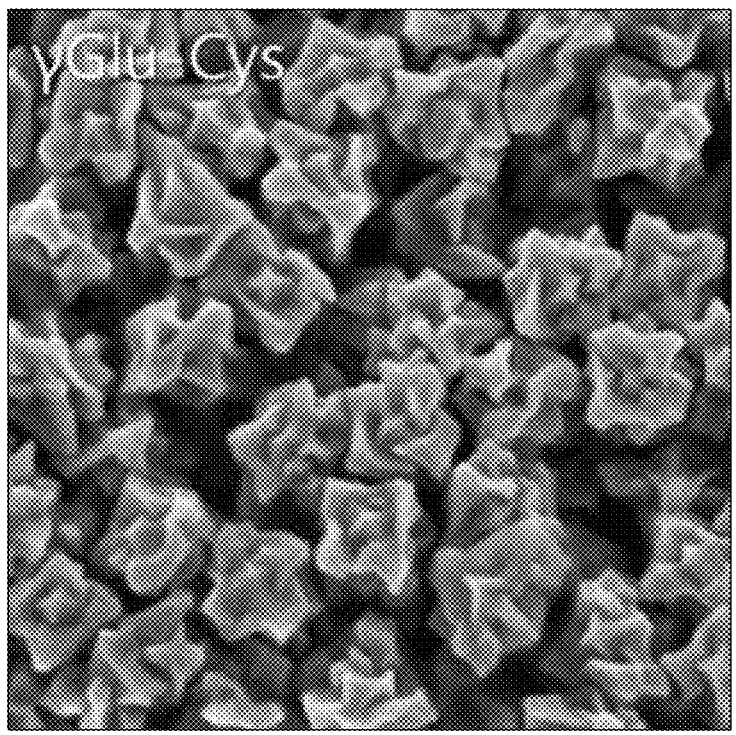
Figure 5B:
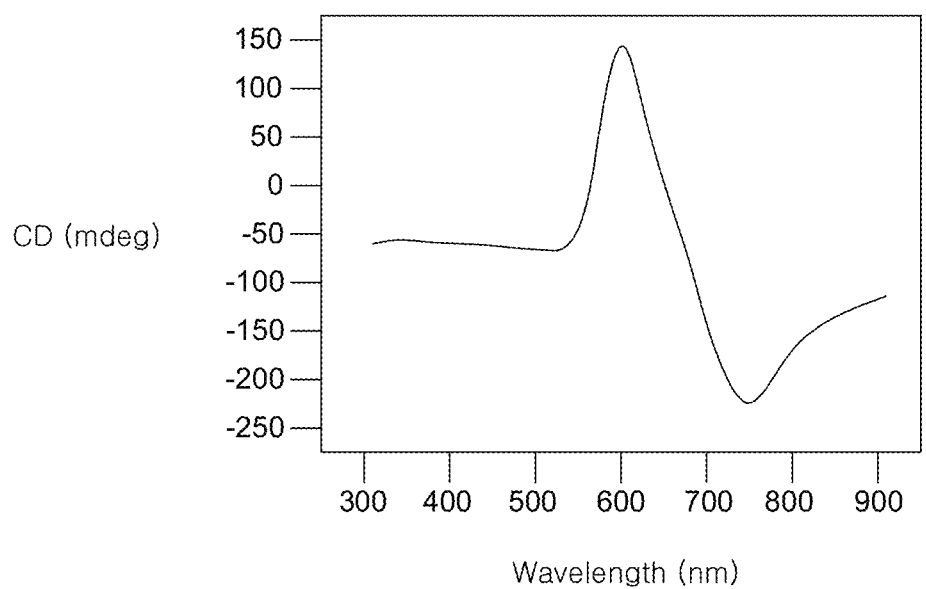
Figure 5C:
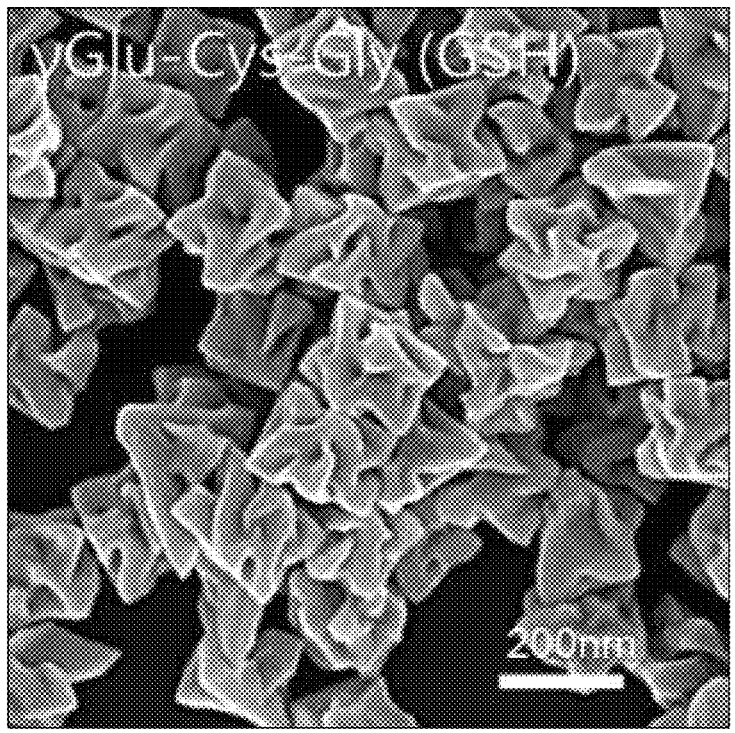
Figure 5C:
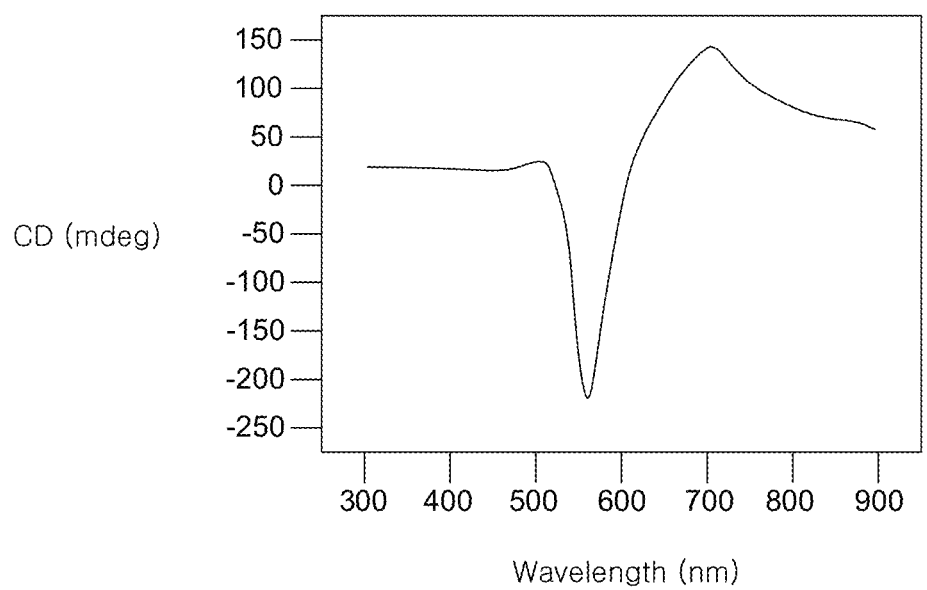

FIGS. 5A to 5D are SEM images and circular dichroism (CD) spectra of a chiral metal nanostructure manufactured using various types of peptides. FIG. 5A illustrates an SEM image and a circular dichroism (CD) spectrum of a metal nanostructure formed using the L-cysteine. FIG. 5B illustrates an SEM image and a circular dichroism (CD) spectrum of a metal nanostructure formed using a dipeptide consisting of γ-glutamate and L-cysteine. FIG. 5C illustrates an SEM image and a circular dichroism (CD) spectrum of a metal nanostructure formed using a tripeptide (L-glutathione) consisting of γ-glutamate, L-cysteine, and glycine.

Figure 5D:
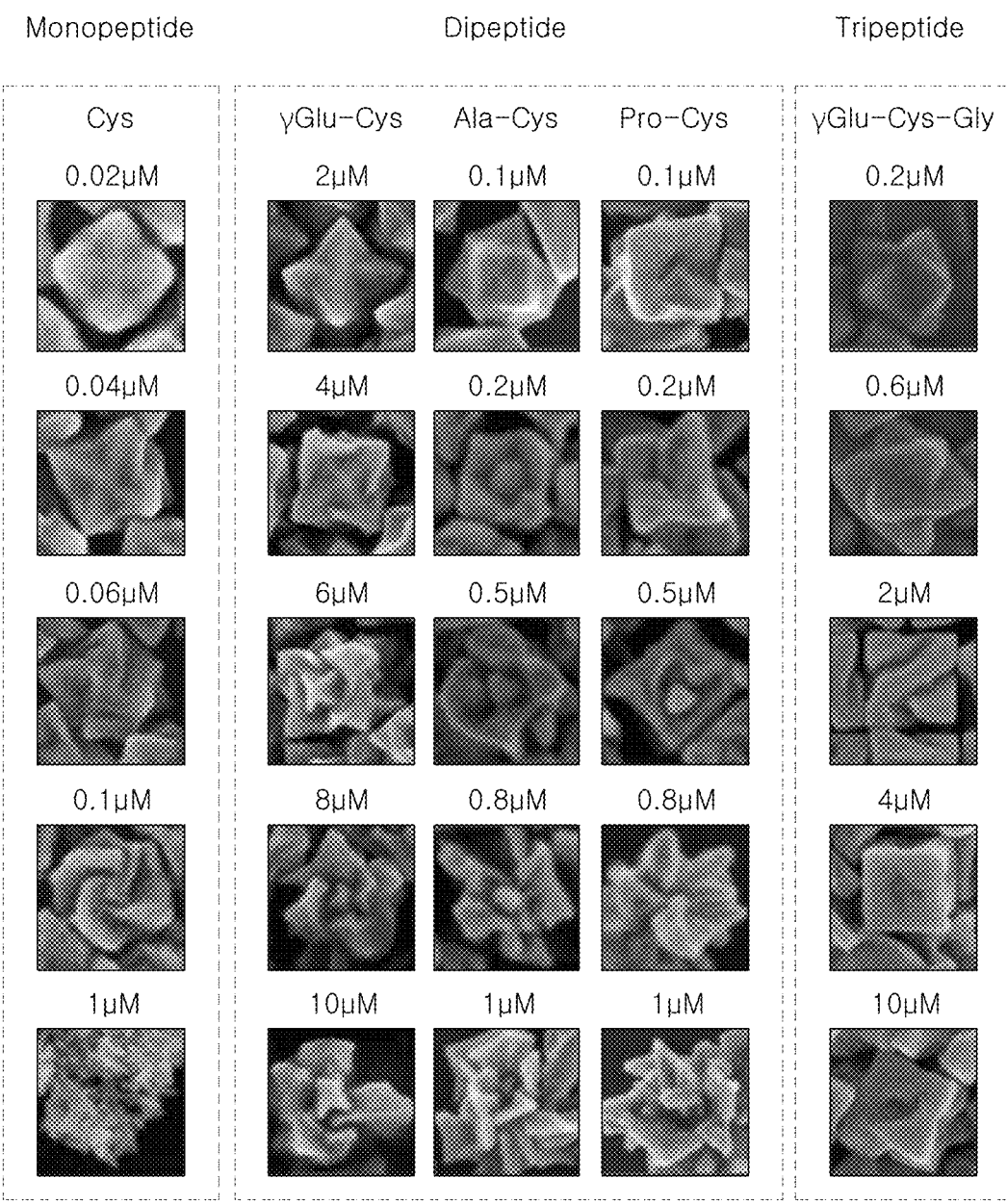

When FIGS. 5A to 5C are compared, it was confirmed that metal nanostructures having totally different chiral structures and optical properties can be formed using different peptides. In the meantime, FIG. 5D illustrates various structures of chiral metal nanostructures formed using various monopeptides, dipeptides, and tripeptides. It was confirmed that the structure of the chiral metal nanostructure varied in accordance with the change of a concentration of the used peptide.

Figure 6A:
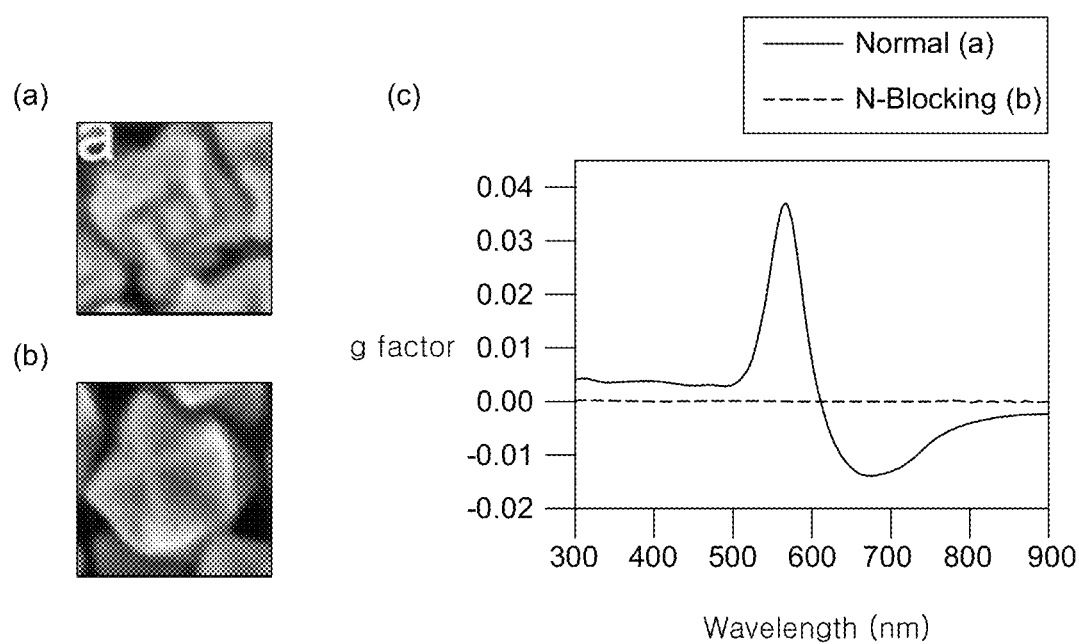
FIGS. 6A and 6B are an SEM image representing that when a structure of peptide is changed, the structure and the optical characteristic of the manufactured chiral metal nanostructure are changed and a graph illustrating a g-factor spectrum according to an embodiment of the present disclosure.
Figure 6B:
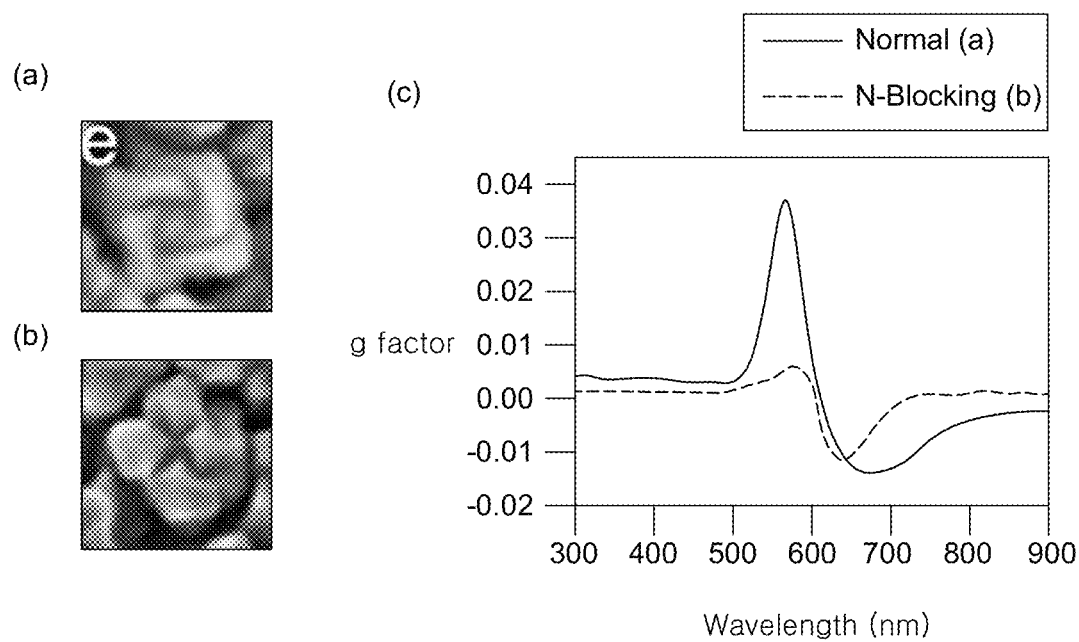

In the meantime, FIGS. 6A and 6B are an SEM image representing that when the structure of peptide is changed, the structure and the optical characteristic of the manufactured chiral metal nanostructure are changed and a graph illustrating a g-factor spectrum.

Referring to FIG. 6A, the chiral metal nanostructure illustrated in FIG. 6A (a) is an SEM image of a chiral metal nanostructure according to Example 1 which is prepared using L-cysteine. Further, the chiral metal nanostructure illustrated in FIG. 6A (b) is an SEM image of a chiral metal nanostructure prepared using N-terminal blocked L-cysteine, that is, L-cysteine in which hydrogen of an amino group is substituted (for example, N-acetyl cysteine). Referring to FIG. 6A (c), it was confirmed that the N-terminal blocked L-cysteine had an achiral property in which a strength of g-factor spectrum is rapidly reduced.

Referring to FIG. 6B, the chiral metal nanostructure illustrated in FIG. 6B (a) is an SEM image of a chiral metal nanostructure according to Example 1 which is prepared using L-cysteine. Further, the chiral metal nanostructure illustrated in FIG. 6B (b) is an SEM image of a chiral metal nanostructure prepared using C-terminal blocked L-cysteine, that is, L-cysteine in which hydrogen of a side chain is substituted (for example, cysteine ethyl ester). Referring to FIG. 6B (c), it was confirmed that the C-terminal blocked L-cysteine had a chiral property in which a strength of g-factor spectrum is reduced.

2. D- and L-Forms of Peptide

In the method for manufacturing a chiral metal nanostructure according to one exemplary embodiment of the present disclosure, the optical characteristic of the prepared chiral metal nanostructure was changed depending on the chiral structure of peptide. When the chiral metal nanostructure was prepared using two peptides which were enantiomers, the formed chiral metal nanostructures may have opposite chiral structures or opposite polarization characteristics.

In order to examine the above description, the chiral metal nanostructure prepared using L-cysteine and D-cysteine which were enantiomers were examined.

As a chiral metal nanostructure prepared using the L-cysteine, the metal nanostructure prepared by Example 1 was examined. The chiral metal nanostructure prepared using D-cysteine was prepared by a method according to Example 3.

Example 3

The chiral metal nanostructure was prepared by the same method as Example 1 except that D-cysteine was used instead of L-cysteine.

Figure 7A:
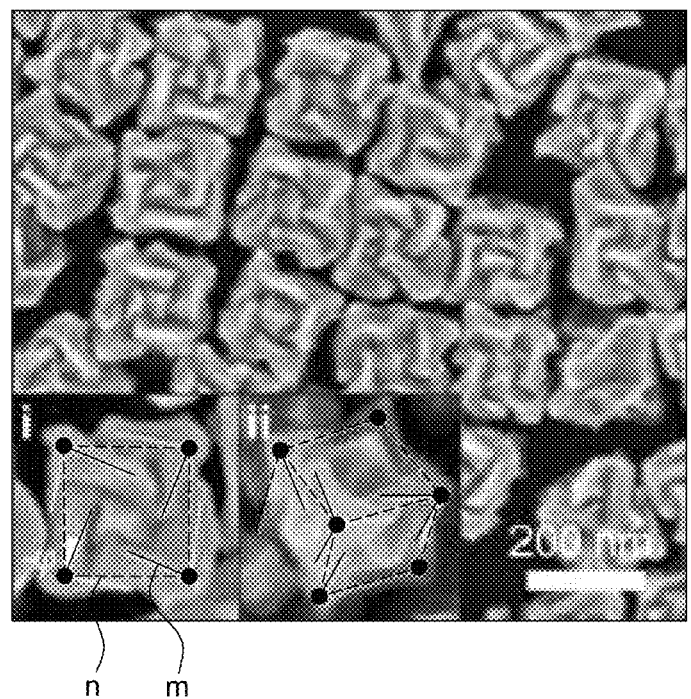
FIG. 7A is an SEM image of a chiral metal nanostructure prepared by Example 1 of the present disclosure.
Figure 7B:
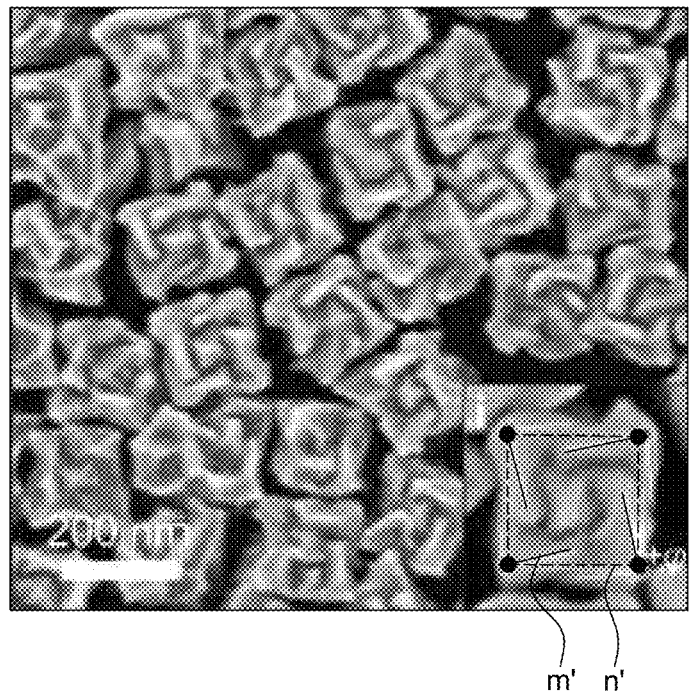
FIG. 7B is an SEM image of a chiral metal nanostructure prepared by Example 3 of the present disclosure.

FIG. 7A is an SEM image of a chiral metal nanostructure prepared by Example 1. FIG. 7B is an SEM image of a chiral metal nanostructure prepared by Example 3.

Referring to FIG. 7A, the chiral metal nanostructure formed using L-cysteine had a twisted corner. Specifically, the chiral metal nanostructure illustrated in FIG. 7A had a corner m which was rotated by $-\varphi$ degree from a straight line n obtained by connecting vertexes. Differently from this, the chiral metal nanostructure illustrated in FIG. 7B had a corner m' which was rotated by $+\varphi$ degree from a straight line n' obtained by connecting vertexes. That is, it was confirmed that the chiral metal nanostructure prepared using L-cysteine and the chiral metal nanostructure prepared using D-cysteine had chiral structures which rotate in opposite directions.

Figure 7C:
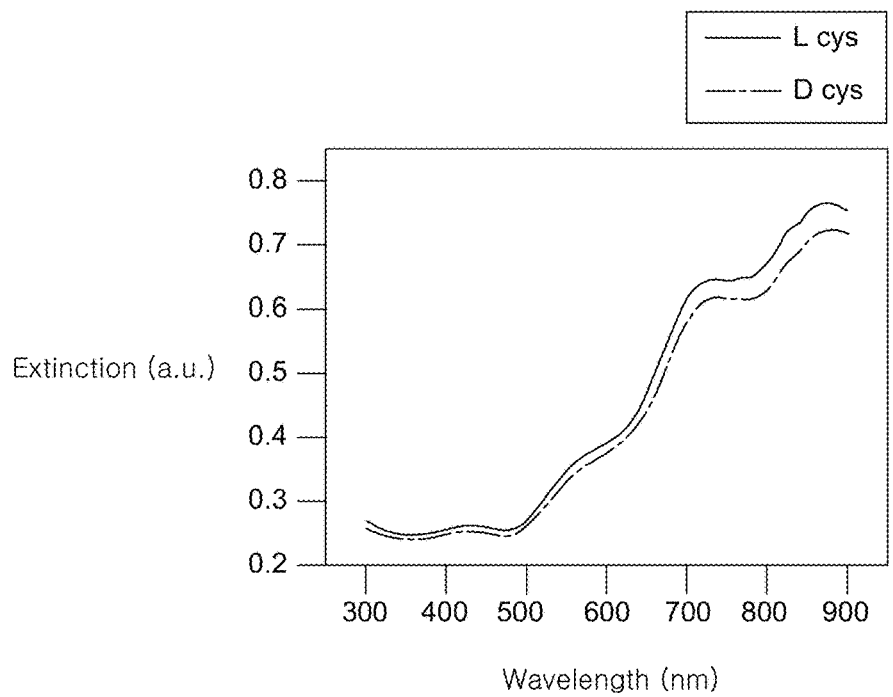
FIG. 7C is a graph illustrating an absorbance spectrum of a chiral metal nanostructure prepared by Examples 1 and 3 of the present disclosure.

FIG. 7C is a graph illustrating an absorbance spectrum of a chiral metal nanostructure prepared by Examples 1 and 3.

Referring to FIG. 7C, it was confirmed that the metal nanostructures using L-cysteine and D-cysteine which were enantiomers had similar absorbance in a wavelength region.

Figure 7D:
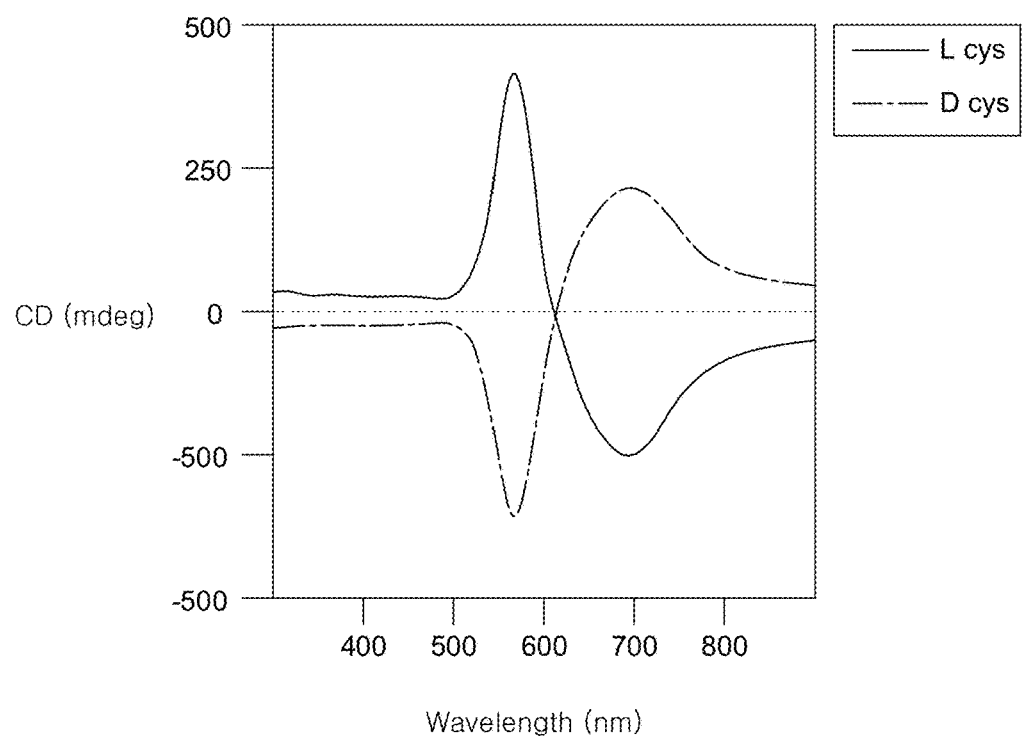
FIG. 7D is a graph illustrating a circular dichroism (CD) spectrum of a chiral metal nanostructure prepared by Examples 1 and 3 of this disclosure.

FIG. 7D is a graph illustrating a circular dichroism (CD) spectrum of a chiral metal nanostructure prepared by Examples 1 and 3.

Referring to FIG. 7D, the chiral metal nanostructure prepared by Example 1 exhibited an absorption spectrum of a left circular polarization at 569 nm and a right circular polarization at 699 nm. In contrast, the chiral metal nanostructure prepared by Example 3 exhibited an absorption spectrum of a right circular polarization at 569 nm and a left circular polarization at 699 nm. That is, it was confirmed that both the chiral metal nanostructure prepared using L-cysteine and the chiral metal nanostructure prepared using D-cysteine had the same maximum peak and opposite polarization characteristics at 569 nm and 699 nm.

3. Content Ratio of D- and L-Forms of Peptide

In the method for manufacturing a chiral metal nanostructure according to one exemplary embodiment of the present disclosure, the chiral structure and the optical characteristic of the prepared chiral metal nanostructure may vary depending on a mixing ratio of two peptides which are enantiomers. That is, the metal nanostructure having various chiral structures may be formed by adjusting a mixing ratio of two peptides which are enantiomers.

In order to examine the above description, the chiral metal nanostructure was prepared while changing a content ratio of L-cysteine and D-cysteine which were enantiomers. Specifically, the chiral metal nanostructure was prepared while changing a content ratio of L-cysteine and D-cysteine to 1:1, 2:1, 3:1, 1:2, and 1:3.

Figure 8A:
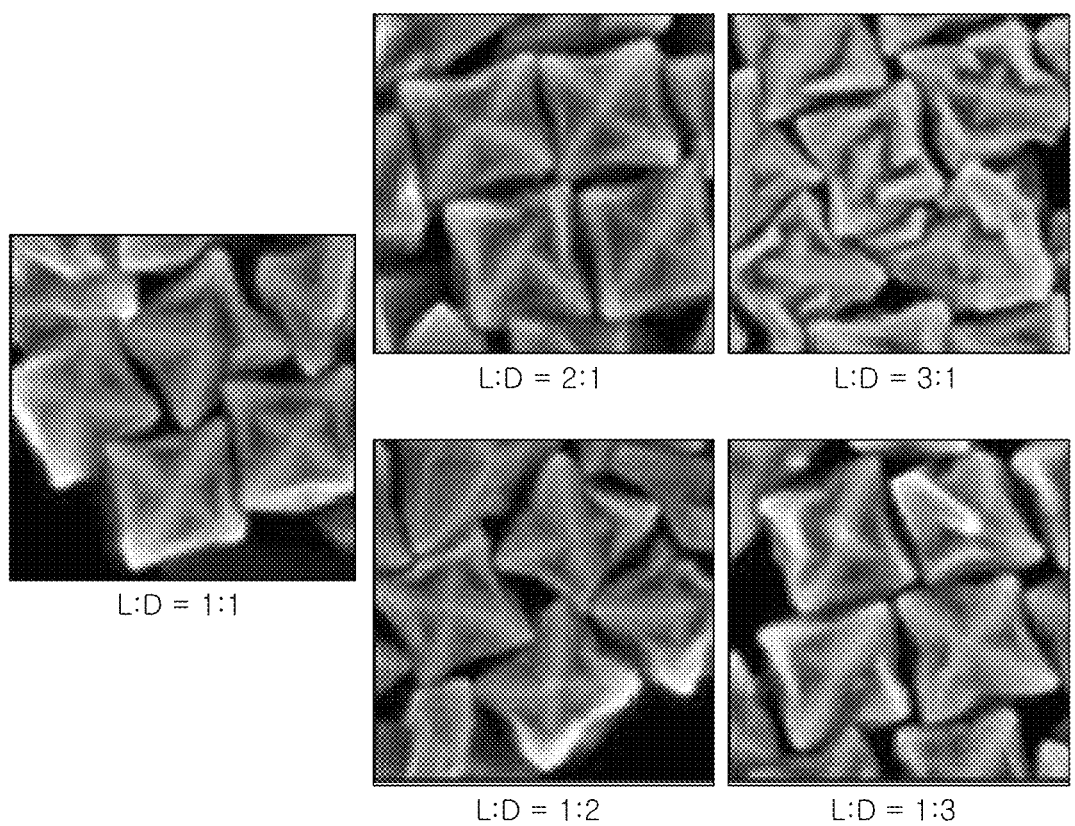
FIGS. 8A and 8B are an SEM image representing that when a content ratio of L-cysteine and D-cysteine is changed, the structure and the optical characteristic of the manufactured chiral metal nanostructure are changed and a graph illustrating a g-factor spectrum according to an embodiment of the present disclosure.
Figure 8B:
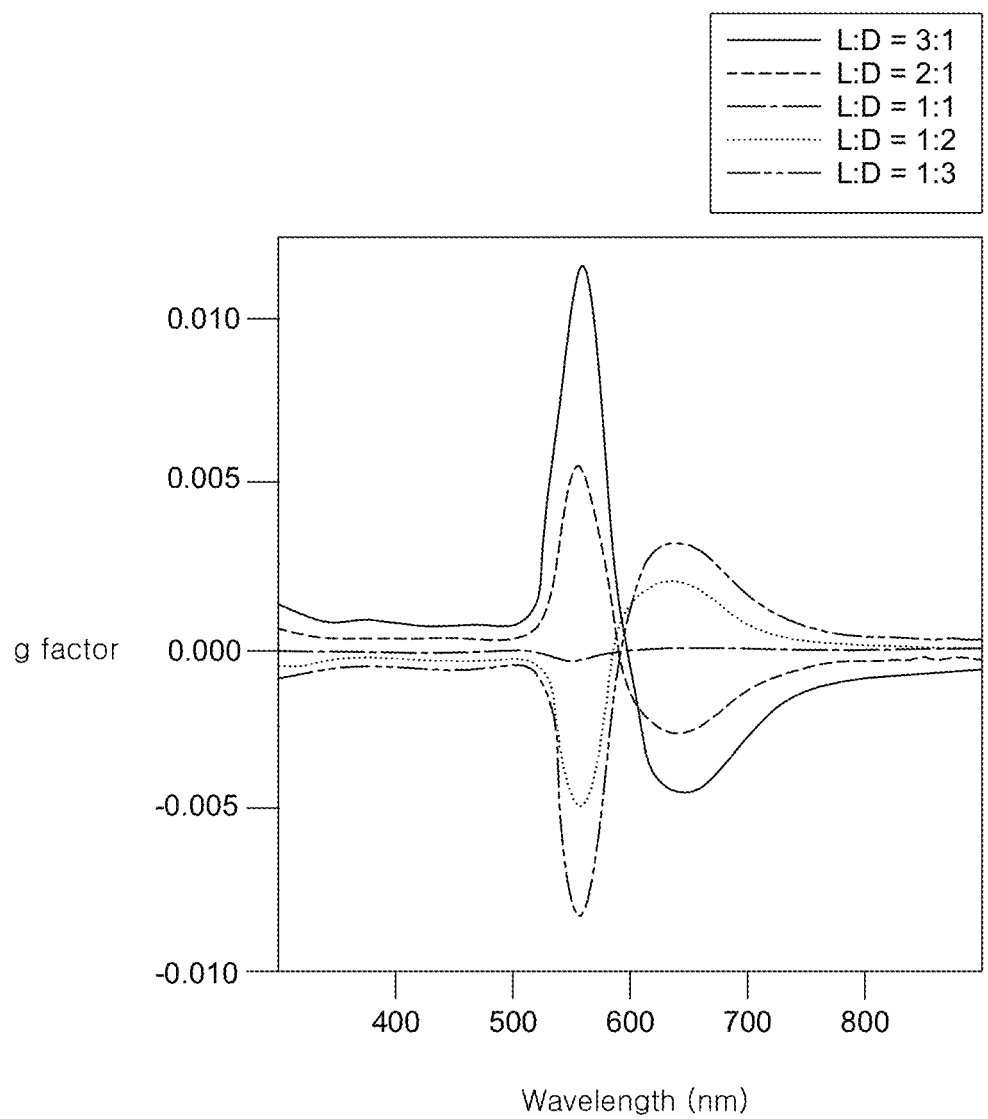

In the meantime, FIGS. 8A and 8B are an SEM image representing that when a content ratio of L-cysteine and D-cysteine is changed, the structure and the optical characteristic of the prepared chiral metal nanostructure are changed and a graph illustrating a g-factor spectrum.

Referring to FIG. 8A, it was confirmed that when the content ratio of the L-cysteine and the D-cysteine having opposite chiral structures was changed, the structure of the prepared metal nanostructure was also changed. Specifically, in the case of a racemic mixing state in which the content ratio of the L-cysteine and the D-cysteine is 1:1, the corner of the prepared metal nanostructure was formed to be substantially parallel to a corner of the initial metal seed particle so that a twisted corner was not formed. In this case, it was confirmed that the chiral of the metal nanostructure disappeared and the metal nanostructure was formed to have an achiral structure.

Further, referring to FIG. 8B, the chiral of the metal nanostructure may be quantitatively adjusted by changing a content ratio of the L-cysteine and the D-cysteine having opposite chiral structures. That is, the strength of the g-factor follows the property of more peptides between the L-cysteine and the D-cysteine. Similarly to FIG. 8A, it was confirmed that in the case of a racemic mixing state in which the content ratio of the L-cysteine and the D-cysteine was 1:1, the g-factor had a value close to 0 in the most of the wavelength region.

4. Shape of Metal Seed Particle

In the method for manufacturing a chiral metal nanostructure according to one exemplary embodiment of the present disclosure, the chiral structure and the optical characteristic of the prepared chiral metal nanostructure may vary depending on the shape of the metal seed particle. That is, the metal nanostructure having various chiral structures may be formed by changing a shape of the metal seed particle injected to the second mixture solution.

In order to examine the above description, a metal nanostructure was formed by changing a shape of the metal nanostructure. Specifically, the above-described Example 2 in which a cube metal particle was used as a metal seed particle and Example 4 in which an octahedron metal particle was used as a metal seed particle were compared. Example 4 will be specifically described below.

Example 4

The chiral metal nanostructure was prepared by the same method as Example 2 except that the octahedron metal seed particle was used instead of the cube metal seed particle. That is, in Example 4, the octahedron metal seed particle was used as a metal seed particle and L-glutathione was used as a peptide.

Figure 9A:
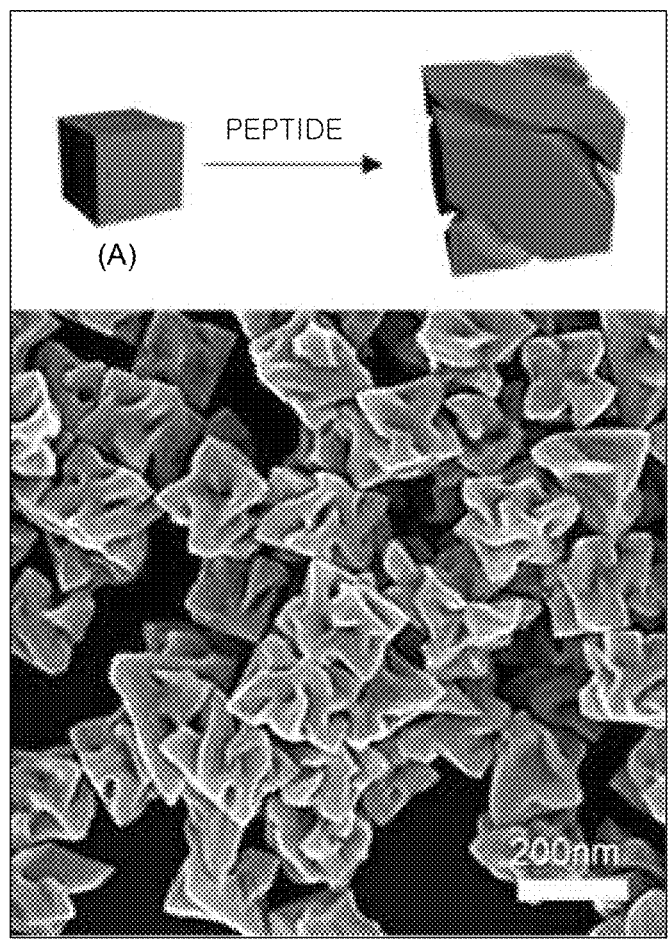
FIG. 9A is a schematic diagram and an SEM image of a chiral metal nanostructure prepared by Example 2 of the present disclosure.
Figure 9B:
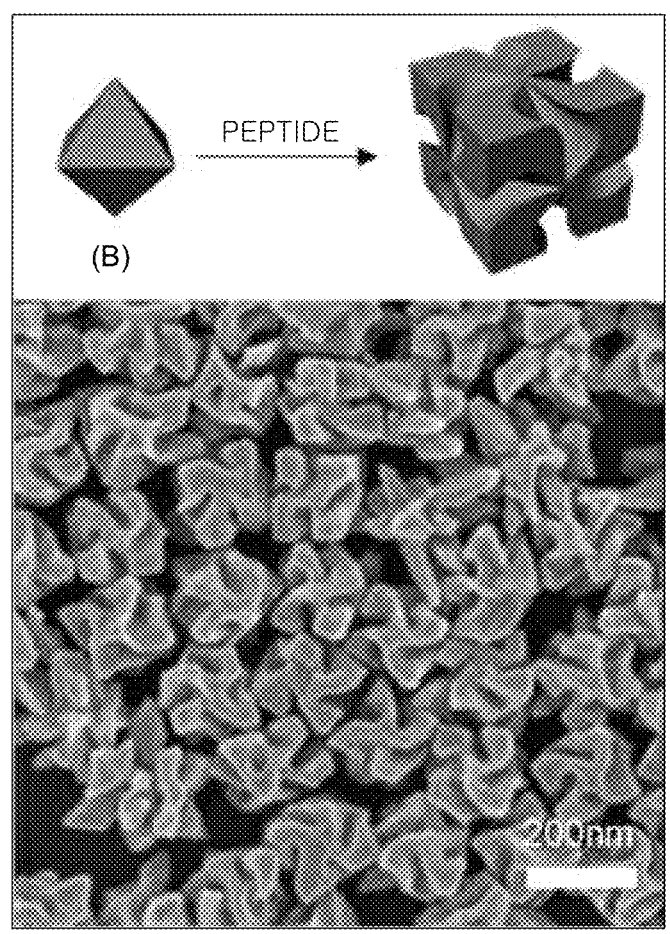
FIG. 9B is a schematic diagram and an SEM image of a chiral metal nanostructure prepared by Example 4 of the present disclosure.
Figure 9C:
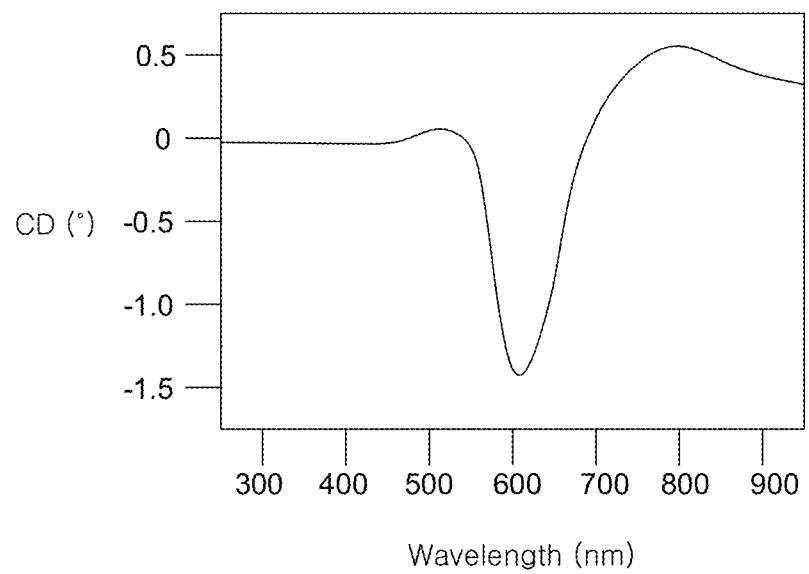
FIG. 9C is a graph illustrating a circular dichroism (CD) spectrum of a chiral metal nanostructure prepared by Example 4 of the present disclosure.
Figure 9D:
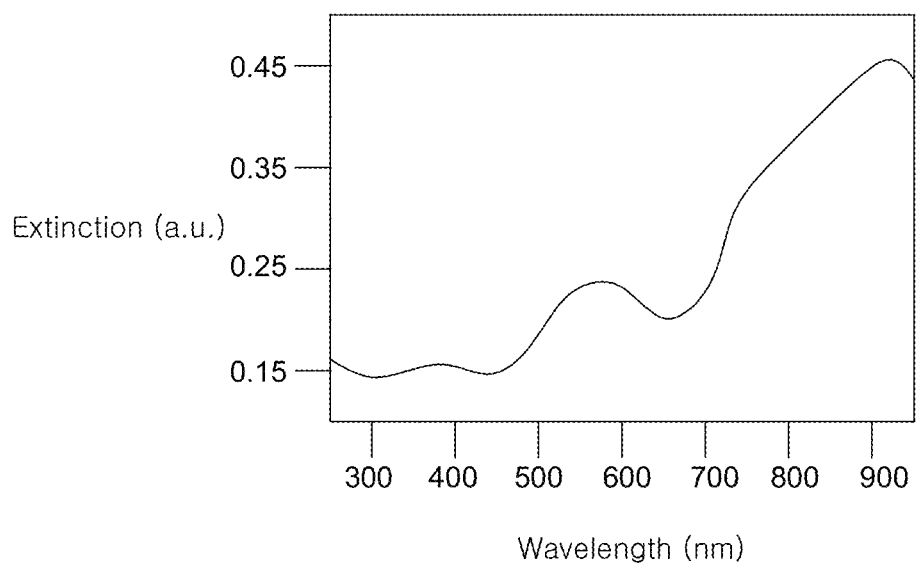
FIG. 9D is a graph illustrating an absorbance spectrum of a chiral metal nanostructure prepared by Example 4 of the present disclosure.

FIG. 9A is a schematic diagram and an SEM image of a chiral metal nanostructure prepared by Example 2. FIG. 9B is a schematic diagram and an SEM image of a chiral metal nanostructure prepared by Example 4. FIG. 9C is a graph illustrating a circular dichroism (CD) spectrum of a chiral metal nanostructure prepared by Example 4. FIG. 9D is a graph illustrating an absorbance spectrum of a chiral metal nanostructure prepared by Example 4. Referring to FIGS. 9C and 9D, it was confirmed that the metal nanostructure having different optical properties was formed by changing the shape of the metal seed particle.

Referring to FIGS. 9A and 9B, it was confirmed that when metal seed particles having different shapes were used, the metal nanostructures having different chiral structures could be formed after the growth of the metal.

More specifically, when the cube metal seed particle is used, a metal nanostructure including a concave portion formed to be connected to two or more surfaces may be formed. Further, when an octahedron metal seed particle was used, a metal nanostructure which included a concave portion commonly formed on two surfaces and has a twisted corner may be formed.

Figure 9E:
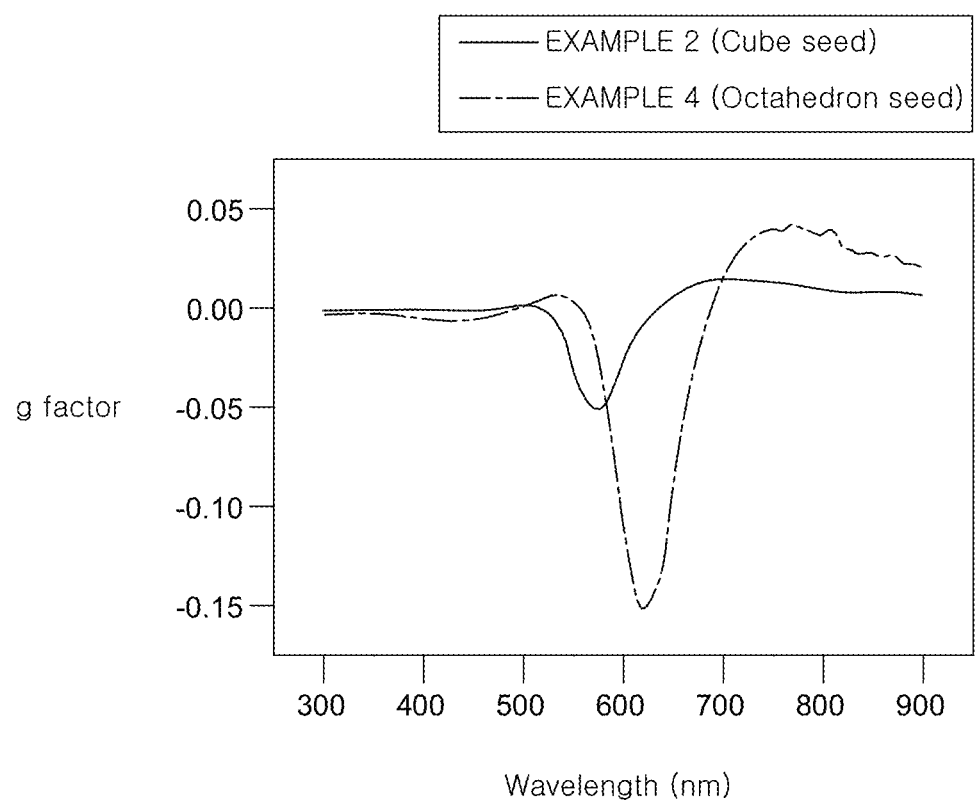
FIG. 9E is a graph illustrating a g-factor spectrum of a chiral metal nanostructure prepared by Examples 2 and 4 of the present disclosure.

FIG. 9E is a graph illustrating a g-factor spectrum of a chiral metal nanostructure prepared by Examples 2 and 4.

Referring to FIG. 9E, it was confirmed that when the octahedron metal seed particle was used, the g-factor of the initially formed metal nanostructure was larger than that the case when the cube metal seed particle was used.

5. Concentration of Metal Seed Particle

In the method for manufacturing a chiral metal nanostructure according to one exemplary embodiment of the present disclosure, the chiral structure and the optical characteristic of the prepared chiral metal nanostructure may vary depending on a concentration of a metal seed particle. That is, the metal nanostructure having various chiral structures may be formed by changing a content of the metal seed particle injected to the second mixture solution.

In order to examine the above-description, a metal nanostructure was formed by changing a content of the metal seed particle injected into the second mixture solution.

Specifically, in Example 4 in which the octahedron metal particle was used as a metal seed particle and L-glutathione was used as a peptide, the metal nanostructure was prepared while changing the concentration of the metal seed particle.

Figure 10:
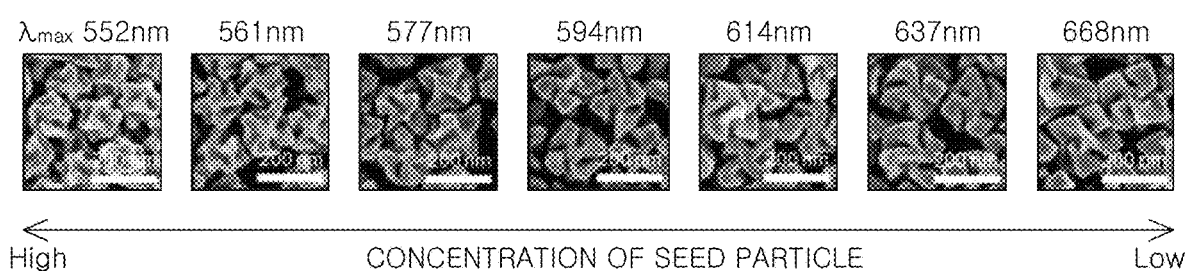
FIG. 10 is an SEM image of a chiral metal nanostructure manufactured by varying a concentration of a metal seed particle according to an embodiment of the present disclosure.

FIG. 10 is an SEM image of a chiral metal nanostructure manufactured by varying a concentration of a metal seed particle. In FIG. 10, a maximum absorption wavelength in a circular dichroism (CD) spectrum was also denoted.

Referring to FIG. 10, it was confirmed that as a concentration of the seed increased, that is, as the amount of the seed particles injected into the second mixture solution increased, the particle size of the prepared metal nanostructure was smaller. It was further confirmed that as the concentration of the seed was reduced, that is, as the amount of the seed particles injected into the second mixture solution was reduced, the particle size of the prepared metal nanostructure was larger. Since the metal precursor in the second mixture solution is limited, when the concentration of the metal seed particle is low, the amount of grown metals per one metal seed particle is increased. Therefore, larger metal nanostructure particles may be formed.

In the meantime, when the size of the metal nanostructure was changed, a plasmon resonance of the metal nanostructure was changed so that red shift was generated. That is, it was confirmed that as the size of the metal nanostructure was increased, the maximum absorption wavelength in the circular dichroism (CD) spectrum moved to a red wavelength region.

6. Growth Time of Metal

In the method for manufacturing a chiral metal nanostructure according to one exemplary embodiment of the present disclosure, a chiral structure of the prepared chiral metal nanostructure may vary depending on a growth time of a metal. That is, the metal nanostructure having various chiral structures may be formed by adjusting a response time after injecting the metal seed particle into the second mixture solution.

Specifically, in the method for manufacturing a chiral metal nanostructure according to Examples 2 and 4, the metal nanostructure was prepared by varying the metal growth time after injecting the metal seed particle into the second mixture solution. In this case, FIG. 11 is an SEM image of a chiral metal nanostructure manufactured by changing a metal growth time in Examples 2 and 4.

Figure 11:
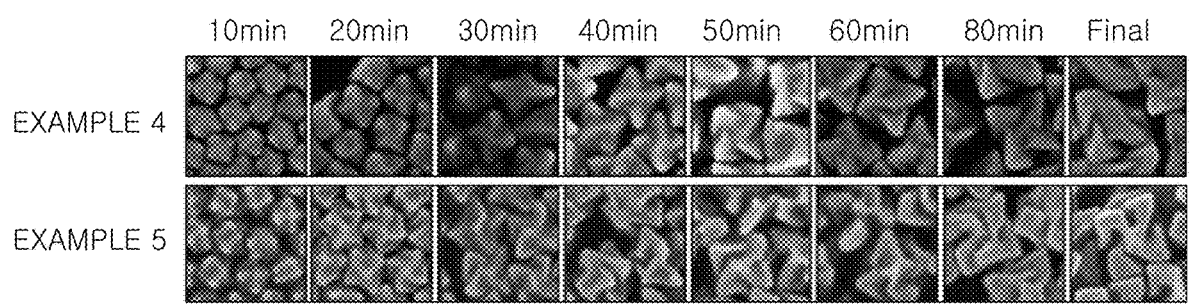
FIG. 11 is an SEM image of a chiral metal nanostructure manufactured by changing a metal growth time in Examples 2 and 4 of the present disclosure.

Referring to FIG. 11, it was confirmed that as the time elapsed, a chiral structure in which the corner further protrudes was formed.

The exemplary embodiments of the present disclosure can also be described as follows:

According to an aspect of the present disclosure, a method for manufacturing a metal nanostructure comprises: preparing a first mixture solution by mixing a metal precursor, a surfactant, and a reducing agent; preparing a second mixture solution by adding a peptide to the first mixture solution; and preparing a metal nanostructure having a chiral structure by adding a metal seed particle to the second mixture solution to grow the metal.

The preparing of a first mixture solution may include preparing a solution containing the surfactant; and mixing the metal precursor and the reducing agent in the solution.

The metal precursor may be a precursor including at least one of gold, silver, and copper.

The peptide may include one or more selected from the group consisting of cysteine (Cys), glutamate (Glu), alanine (Ala), glycine (Gly), penicillamine, histidine, lysine, ornithine, arginine, aspartic acid, glutamic acid, asparagine, glutathione, and glutamine.

The peptide may be a monopeptide, a dipeptide, or a tripeptide.

The peptide may comprise a thiol group.

The peptide may comprise both a D-form isomer and an L-form isomer which are enantiomers.

A size of the metal seed particle may be 1 nm to 100 nm.

A particle size of the metal nanostructure may be 10 nm to 500 nm.

The surfactant may be cetyltrimethylammonium bromide and the reducing agent may be ascorbic acid.

According to another aspect of the present disclosure, a metal nanostructure has a chiral structure and a particle size of 10 nm to 500 nm.

The metal nanostructure may comprise a concave portion and a convex portion and the concave portion and the convex portion may extend to be bent in one direction.

The concave portion may be formed to be connected to an adjacent surface and the concave portion may be formed to extend to at least two surfaces.

The convex portion may extend to be bent in the same direction with respect to a vertex.

The metal nanostructure may have a helicoid shape in which a corner is twisted in one direction.

The metal nanostructure may be formed by growing a metal from a metal seed particle having a size of 1 nm to 100 nm and a corner of the metal nanostructure may rotate at a predetermined angle with respect to the corner of the metal seed particle.

Although the exemplary embodiments of the present disclosure have been described in detail with reference to the accompanying drawings, the present disclosure is not limited thereto and may be embodied in many different forms without departing from the technical concept of the present disclosure. Therefore, the exemplary embodiments of the present disclosure are provided for illustrative purposes only but not intended to limit the technical concept of the present disclosure. The scope of the technical concept of the present disclosure is not limited thereto. Therefore, it should be understood that the above-described exemplary embodiments are illustrative in all aspects and do not limit the present disclosure. The protective scope of the present disclosure should be construed based on the following claims, and all the technical concepts in the equivalent scope thereof should be construed as falling within the scope of the present disclosure.

What is claimed is:

1. A method for manufacturing a metal nanostructure, the method comprising:
    preparing a first mixture solution by mixing a metal precursor, a surfactant, and a reducing agent;
    preparing a second mixture solution by adding a peptide to the first mixture solution; and
    preparing a metal nanostructure having a chiral structure by adding a metal seed particle to the second mixture solution to grow the metal nanostructure,
    wherein when the metal seed particle is added to the second mixture solution in the preparing the metal nanostructure, the peptide is regioselectively adsorbed on the surface of the metal seed particle,
    wherein the metal nanostructure is synthesized at a room temperature,
    wherein the chiral structure means a structure in which the metal nanostructure does not overlap with its mirror image, and a shape which is twisted in one direction as asymmetric structure.

2. The method according to claim 1, wherein the preparing of a first mixture solution includes:
    preparing a solution containing the surfactant; and
    mixing the metal precursor and the reducing agent in the solution.

3. The method according to claim 1, wherein the metal precursor is a precursor including at least one of gold, silver, and copper.

4. The method according to claim 1, wherein the peptide comprises a thiol-group.

5. The method according to claim 1, wherein a size of the metal seed particle is 1 nm to 100 nm.

6. The method according to claim 1, wherein a particle size of the metal nanostructure is 10 nm to 500 nm.

7. The method according to claim 1, wherein the surfactant is cetyltrimethylammonium bromide and the reducing agent is ascorbic acid.

* * * * *